United States Patent [19]

Hiji

[11] Patent Number: 4,761,286

[45] Date of Patent: Aug. 2, 1988

[54] INTESTINAL ABSORPTION INHIBITING AGENT

[76] Inventor: Yasutake Hiji, c/o Tottori University School of Medicine, 86, Nishi-machi, Yonago-shi, Tottori-ken, Japan

[21] Appl. No.: 8,081

[22] Filed: Jan. 27, 1987

Related U.S. Application Data

[63] Continuation of Ser. No. 745,161, Jun. 17, 1985, abandoned.

[30] Foreign Application Priority Data

Jun. 18, 1984 [JP] Japan ................................ 59-124826

[51] Int. Cl.$^4$ ............................................. A61K 35/78
[52] U.S. Cl. ................................... 424/195.1; 426/804
[58] Field of Search ...................... 424/195.1; 426/804

[56] References Cited

PUBLICATIONS

Chem. Abs. 95: 148281z, 1981.
Chem. Abs. 77: 101973q, 1972.
Chem. Abs. 79: 124843c, 1973.
Steinmetz, Codex Vegetablis 1957, No. 533.

Primary Examiner—John Rollins
Attorney, Agent, or Firm—Armstrong, Nikaido, Marmelstein & Kubovcik

[57] ABSTRACT

*Gymnema sylvestre* is added to glucose for inhibiting absorption of the glucose through intestine, whereby the increase in calorie intake which usually arises from taking of glucose-containing foodstuffs can be restrained at a low level.

12 Claims, 3 Drawing Sheets

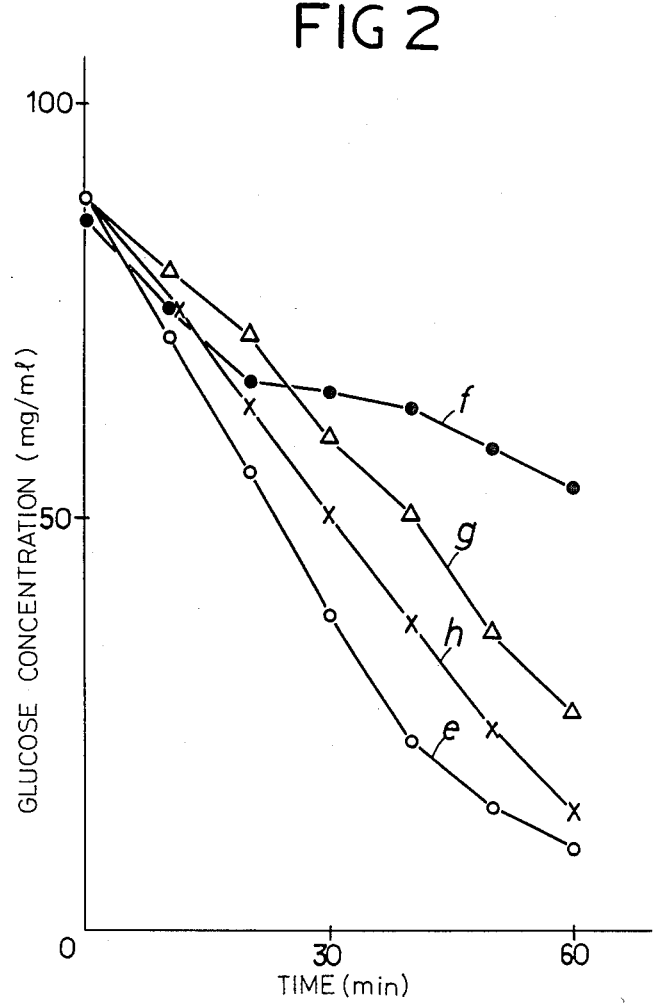

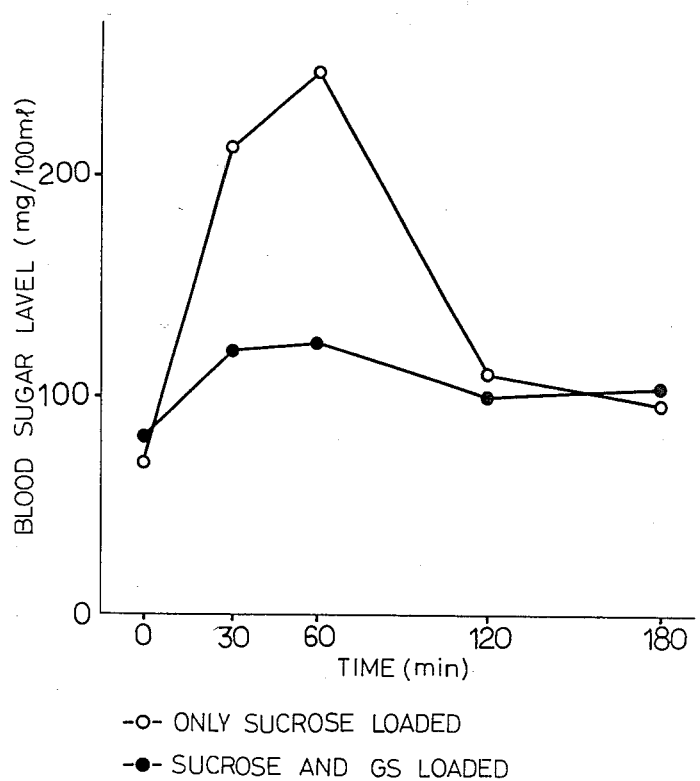

INTESTINAL ABSORPTION INHIBITING AGENT

This application is a continuation of application Ser. No. 745,161, filed June 17, 1985, now abandoned.

BACKGROUND OF THE INVENTION

The present invention relates to low-caloric foods and beverages.

As the food life becomes luxurious, people tend to take more foods and beverages than they need, making the obesity notable among them. In the present age where the preference for sweetness is strong, the amount of intake of carbohydrates is more serious for preventing the obesity than that of lipids, and therefore, it is necessary not to take sugar, starch and the like excessively.

However, restricting the intake of sweet foods and processed starch foods results in frustration and stress build up.

If, in view of the fact that all the carbohydrates are decomposed to glucose and then absorbed from the intestinal tract, it is arranged to inhibit absorption of glucose through the intestinal tract, this will result in control of the amount of intake of carbohydrates, enabling the obesity to be prevented while avoiding frustration.

Researches have been made heretofore from the above viewpoint, and it has been considered that a certain kind of polysaccharide (for example, dextran) has an effect of controlling the increase in blood sugar content which arises from intake of sugar and that a low-caloric food or beverage effective for preventing obesity may be obtained by adding such polysaccharide to sugar and the like.

However, it has been found that such kind of polysaccharide does not inhibit absorption of sugar and therefore glucose through the intestinal tract and even if this polysaccharide is present, glucose is normally absorbed from the intestinal tract. Thus the polysaccharide contributes nothing to reduction of the calorie intake of sugar.

The Food Indication Permission Standard established by the Ministry of Public Welfare of Japan defines "a low-calorie food" as—a food of which calorie intake is less than 50% of that of an ordinary food of the same kind—. Even if the increase in blood sugar content is reduced by 50% from a normal level by use of the polysaccharide, this does not directly lead to reduction of the calorie intake by one half. The reason is that if a hormone (for example, insulin) is secreted in a large amount, the blood sugar level is seemingly reduced.

Accordingly, even if only reduction of the blood sugar level is taken into consideration, a low-calorie food or beverage effective for preventing obesity cannot be provided.

SUMMARY OF THE INVENTION

In view of the above-mentioned circumstances, the present invention aims at providing an agent for inhibiting absorption of glucose from the intestinal tract, which has been developed by directly measuring the amount of glucose absorbed from the intestinal tract without reduction of the blood sugar level being taken into consideration.

The inventor conducted many studies with a view to attaining the above object, and as the result, he found that when *Gymnema sylvestre* (hereinafter referred to as "GS") extracted from leaves of plants belonging to the family of asclepiadaceae which grow naturally in India, Africa and China is added to a carbohydrate, glucose absorption through the intestinal tract can be inhibited.

The above-mentioned GS is obtainable by the following steps. That is, dried leaves of the family plant are immersed in an aqueous solution at 60° C. for about 5 hours and combined extract was precipitated by adjusting pH to 3.0 with sulfuric acid. Precipitate was collected by centrifugation at 10,000 rpm for 10 min and dissolved in ethanol. Extraction solvable was collected by centrifugation and concentrated by evaporation. After two parts of acetone was added to this extraction, supernatant was dried under the reduced pressure. The residue was extracted several tens times with boiling diethylcarbonate and GS was crystallized from the solvent. As a result, there is obtained about 13 g of GS per Kg of the dried leaves. From the results of analysis of the extraction product by a flamed ionized detector, it was found that the product contains many components, of which two special components are considered to be especially effective and each of contents of the two effective components is 10%. These are included in glycosides.

The inventor also found that if GS is added to glucose in such an amount of 1/50–3/10 (weight ratio), the remarkable effect of inhibiting the intestinal glucose absorption is exhibited. Maximum absorption inhibition ratio is about 50%, and the inhibiting effect lasts for more than 2 hours.

Accordingly, in case of the production of sweet foodstuffs, if GS is added in the above-mentioned range of weight ratio at the time of or before or after addition of glucose to the foodstuffs during the production process, there can be obtained low-calorie foodstuffs. GS may be added in any arbitrary manner which may be selected as appropriate for the production process of respective foodstuffs.

Furthermore, even if the concentration of GS is low, so far as the weight ratio is within the above-mentioned range, the intended intestinal glucose absorption inhibiting effect can be attained. Therefore, in addition to the above mode of use in which the GS extraction is added after concentration, there may be employable other modes of use, for example, such a mode that GS-containing leaves of the above family plants are immersed in hot water like tea leaves and the extract is drunk everyday or that GS extraction is taken as a healthful medicine simultaneously with or after or before intake of an ordinary food or beverage. Accordingly, it is believed that GS will make a variety of contributions to social welfare.

As is apparent from the foregoing description, according to the present invention, since a high intestinal absorption inhibiting effect is attained by adding GS to glucose in the above-mentioned specific weight ratio, the obesity can be prevented while avoiding frustration to the sweetness, and low-caloric foods and beverages suitable for diabetic persons can be provided.

Other objects, features and advantages of the present invention will become apparent from the examples given hereinafter.

BRIEF DESCRIPTION OF THE DRAWINGS

FIG. 2 is a graph illustrating the relationship between the time and the glucose concentration.

FIG. 3 is a graph illustrating the change in blood sugar level induced by intake of sucrose and sucrose added with GS with the passage of time.

DETAILED DESCRIPTION OF THE PREFERRED EMBODIMENTS

Example I

Sample solutions were prepared by adding GS to glucose in various ratios, and the glucose intestinal absorption inhibition assay was carried out in the following manner.

Wistar strain rats were peritoneally anesthetized, and only the intestinal tract of each rat was cut out without damaging blood vessels and nerves and the sample solution was perfused in the intestinal tract from the cut end.

If glucose is introduced into the intestinal tract, a potential difference (active transport induction potential by Na+ion) is caused proportionally to the amount of absorbed glucose between the inside and outside of the small intestinal wall. Accordingly, in this example a calomel electrode was inserted into the intestine to determine this potential difference.

Figure 1A:
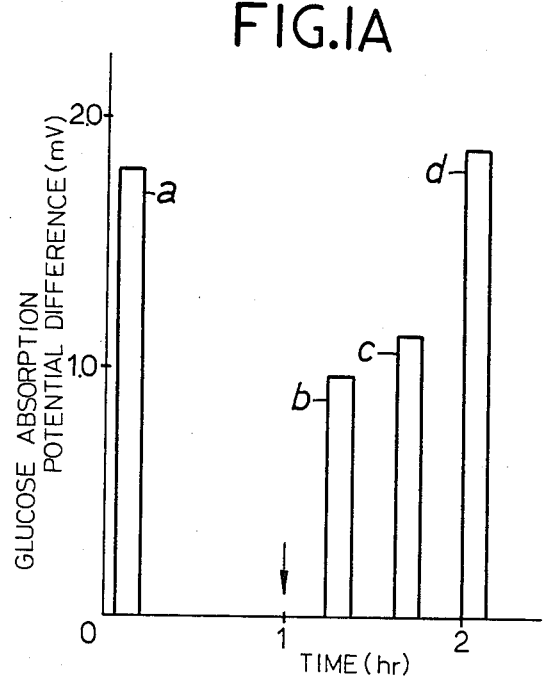
FIG. 1A is a graph illustrating the relationship between the time and the glucose absorption potential difference.

FIG. 1A shows the results of measurement of the potential difference induced by glucose absorption. When a 5 mM glucose solution alone was perfused through the intestine, a potential difference of about 2 mV was induced as indicated by a in FIG. 1A. After perfusion of about 1 hour (the point indicated by the arrow in FIG. 1A), a sample solution with 0.25 mg/ml of GS added to 5 mM glucose was perfused into the intestinal tract. As indicated by b in FIG. 1A, the potential difference was half reduced to be about 1 mV. Then, the potential difference was gradually elevated with the lapse of time as ihdicated by c in FIG. 1A, and after about 1 hour from the point of introduction of the sample solution, the potential difference was restored to about 2 mV as indicated by d in FIG. 1A. This means that the glucose absorption inhibiting effect by GS lasted for 1 hour.

Figure 1B:
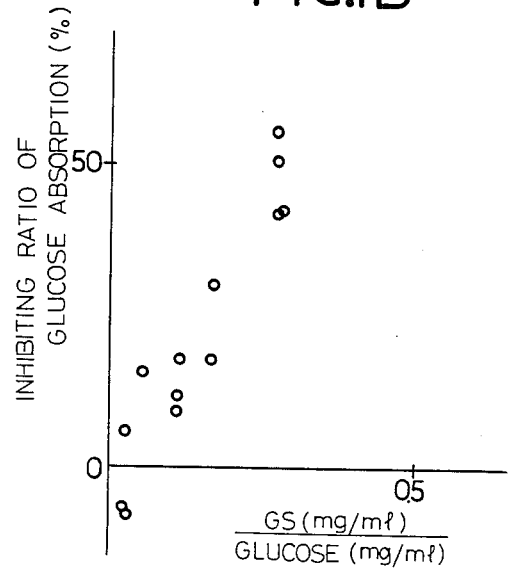
FIG. 1B is a graph illustrating the relationship between the GS/glucose ratio and the glucose absorption inhibition ratio.

FIG. 1B shows the inhibiting effect of GS on the intestinal glucose absorption at some specific ratios of GS to glucose. It is seen from this figure that when the weight ratio of GS to glucose was 0.3, the glucose absorption was reduced to about ½ of a normal level. Although the results obtained at weight ratios of GS to glucose higher than 0.3 are not shown in FIG. 1B, no prominent effect of inhibiting the glucose absorption could be attained at a weight ratio exceeding 0.3.

Example II

A peristaltic pump was connected to the cut end of the intestinal tract of each Wistar strain rat of the same kind as used in Example I, and a sample solution of 30 ml volume was perfused and circulated through the intestinal tract for 1 hour. Intestinal perfusion test was carried out in the following manner for determining the reduction of glucose concentration in the solution with time caused by the glucose contained in the sample solution being absorbed through the intestine. Namely, at each point of 0 minute, 10 minutes, 20 minutes, 30 minutes, 40 minutes, 50 minutes and 60 minutes from the start of perfusion, 0.1 ml of the perfused solution was sampled and the concentration of glucose remaining in the solution was measured by the glucose oxidase method.

The results of the perfusion test are shown in FIG. 2.

In FIG. 2, curve e shows the results obtained when a solution containing 5 mM of glucose alone was perfused. At the point of 60 minutes, most of the glucose was absorbed in the intestinal tract and the residual amount of glucose was only 10 mg/ml.

Curve f shows the results obtained when a sample solution formed by adding 0.25 mg/ml of GS to 5 mM of glucose was perfused. Even at the point of 60 minutes, 55 mg/ml of glucose was left in the sample solution, and this amount was about 5 times the amount of glucose left in the sample solution containing glucose alone.

Curve g shows the results obtained from a perfusion test which was conducted with use of a solution added with 5 mM glucose alone after 30 minutes from the termination of the previous test as shown by curve f while the interior of the intestinal tract was sufficiently washed with Ringer's solution. It is seen that when perfusion was conducted for 60 minutes, the residual amount of glucose was 25 mg/ml and the inhibiting effect by GS of intestinal glucose absorption still endured.

Curve h shows the results of a perfusion test with a solution with 5 mM glucose alone added, which was carried out after passage of 30 minutes from the termination of the test indicated by curve g. This curve shows that when the perfusion was conducted for 50 minutes, the amount of glucose remaining in the solution was 24 mg/ml and the effect of inhibiting intestinal glucose absorption still endured.

This tendency of the intestinal glucose absorption inhibiting effect is well in conformity to the change in glucose absorption potential difference with time illustrated in Example I.

GS can further exhibit the effect of inhibiting the increase in blood sugar level which normally arises when carbohydrates are taken in. The following example evidences such effect of GS.

Example III

The elevation of blood sugar level after the oral sucrose administration was observed periodically. Experimental animals were Wistar strain rats weighing 200–250 g. Used rats were streptozotocin-induced diabetic rats. A dose of 2 g/kg b. w. sucrose was loaded by the stomach sonde and the blood sample was withdrawn from the tail vein at 0, 30, 60, 120 and 180 min., respectively, after the oral administration. Blood sugar content of the sample was measured by the glucose oxidase method. The results of the oral sucrose tolerance test in diabetic rats is shown in FIG. 3. Blood sugar level was elevated until 60 min after sucrose dosage and was settled to the level of the fast within 180 min, while in the case of the administration of sucrose added by 0.2 g/kg b. w. of GS (that is, in the ratio of 1:10 of GS to sucrose), the blood sugar level was suppressed to stay at as low a level as of the fast.

It has been found out by the inventor that more remarkable effects can be seen on the depression of blood sugar level elevation when added to carbohydrates in the form of a mixture with pullulan which is used in low caloric foodstuffs.

I claim:

1. A composition to be ingested by an animal having an intestinal tract as a foodstuff, comprising:
   (a) an aqueous extract of *Gymnema sylvestre*, and
   (b) a food material which is absorbed in the form of glucose by an intestinal tract of an animal having an intestinal tract,
   said extract being present in an amount equaling a weight ratio of from 0.02 to 0.3 to said glucose.

2. The foodstuff composition of claim 1, wherein the food material consists essentially of carbohydrates.

3. The foodstuff composition of claim 1, wherein the food material consists essentialy of glucose.

4. A method of preparing a foodstuff to be ingested by an animal having an intestinal tract comprising:
   (A) preparing an aqueous extract of *Gymnema sylvestre*, and
   (B) mixing said extract with a food material which is absorbed in the form of glucose by an intestinal tract of an animal having an intestinal tract, in a weight ratio of said extract to said glucose which is in the range of 0.02 to 0.3.

5. The method of preparing a foodstuff as set forth in claim 4, wherein the food material consists essentially of carbohydrates.

6. The method of preparing a foodstuff as set forth in claim 4, wherein the food material consists essentially of glucose.

7. A method of reducing the calorie intake value to an animal having an intestinal tract, which is produced by a foodstuff which is ingested by the animal, wherein the foodstuff is absorbed as glucose by the intestinal tract of the animal, comprising:
   (A) orally ingesting a food material which is absorbed by the intestinal tract of an animal having an intestinal tract, and
   (B) orally ingesting an aqueous extract of *Gymnema sylvestre* at a time chosen from about two hours prior to, to just after ingestion of the foodstuff, and in an amount which is effective for inhibiting the absorption of the glucose by the intestinal tract, so as to reduce the caloric intake value to the animal upon the ingestion of the foodstuff.

8. The method of reducing the calorie intake of a foodstuff as in claim 7, wherein the *Gymnema sylvestre* extract is ingested as a component part of the food material.

9. The method of reducing the calorie intake of a foodstuff as in claim 7, wherein the *Gymnema sylvestre* extract is ingested within two hours prior to the ingestion of the food material.

10. The method of reducing the calorie intake of a foodstuff as in claim 7, wherein the *Gymnema sylvestre* extract is ingested at the same time the food material is ingested.

11. The method of reducing the calorie intake of a foodstuff as in claim 7, wherein the *Gymnema sylvestre* extract is ingested just after the food material is ingested.

12. The method of reducing the calorie intake of a foodstuff as in claim 7, wherein the *Gymnema sylvestre* extract is ingested in the form of a tea prepared from *Gymnema sylvestre* leaves.

* * * * *